(12) United States Patent
Alberto et al.

(10) Patent No.: US 8,512,675 B2
(45) Date of Patent: Aug. 20, 2013

(54) **N AND/OR $N^\alpha$ DERIVATIZED, METAL AND ORGANIC PROTECTED L-HISTIDINE FOR COUPLING TO BIOMOLECULES FOR HIGHLY EFFICIENT LABELING WITH $[M(OH_2)_3 (CO)_3]^+$ BY *FAC* COORDINATION**

(75) Inventors: Roger Alberto, Winterthur (CH); Jae Kyoung Pak, Baar-Inwil (CH)

(73) Assignee: Mallinckrodt LLC, Hazelwood, MO (US)

( * ) Notice: Subject to any disclaimer, the term of this patent is extended or adjusted under 35 U.S.C. 154(b) by 1860 days.

(21) Appl. No.: 10/554,331

(22) PCT Filed: Apr. 29, 2004

(86) PCT No.: PCT/EP2004/004683
§ 371 (c)(1),
(2), (4) Date: Oct. 24, 2005

(87) PCT Pub. No.: WO2004/097406
PCT Pub. Date: Nov. 11, 2004

(65) Prior Publication Data
US 2007/0077195 A1 Apr. 5, 2007

(30) Foreign Application Priority Data
Apr. 29, 2003 (EP) ..................... 03076252

(51) Int. Cl.
*A61K 51/00* (2006.01)
*A61M 36/14* (2006.01)

(52) U.S. Cl.
USPC ....... 424/1.69; 424/1.11; 424/1.49; 424/1.65; 424/1.73; 534/14

(58) Field of Classification Search
USPC ............... 424/1.11, 1.37, 1.49, 1.53, 1.65, 424/1.69, 1.73, 9.1; 534/7, 10–14; 544/1, 544/224; 548/100, 300.1
See application file for complete search history.

(56) References Cited

U.S. PATENT DOCUMENTS

| | | | |
|---|---|---|---|
| 5,571,792 | A | 11/1996 | Bolton et al. |
| 5,824,803 | A | 10/1998 | Conrad et al. |
| 6,344,178 | B1 * | 2/2002 | Alberto et al. ............. 424/1.65 |
| 6,926,883 | B1 * | 8/2005 | Dyszlewski et al. ........ 424/1.65 |
| 7,582,295 | B2 * | 9/2009 | Alberto et al. ............. 424/130.1 |

FOREIGN PATENT DOCUMENTS

| | | |
|---|---|---|
| WO | WO 91/07430 | 5/1991 |
| WO | WO 92/00068 | 1/1992 |
| WO | WO 97/26246 | 7/1997 |
| WO | WO 98/48848 | * 11/1998 |
| WO | WO 01/00637 | 1/2001 |
| WO | WO 02/14285 | 2/2002 |

OTHER PUBLICATIONS

Brothers et al, Inorganic Chemistry, 1988, vol. 27, No. 10, pp. 1761-1767.*
Schibli et al (Bioconjugate Chemistry, 2000, vol. 11, pp. 345-351).*
Chu et al (Nuclear Techniques, May 2002, Vo. 25, No. 5, pp. 361-366).*
Van Staveren, Zuerich, Zurich, CH-8057, Switz, Organic & Biomolecular Chemistry, 2004, Vo. 2, No. 18, pp. 2593-2603.*
Crestfield et al., Alkylation and Identification of the Histidine Residues at the Active site of Ribonuclease*, The Journal of Biological Chemistry, vol. 238, No. 7, Jul. 1963, pp. 2413-2420.
Jain et al., Regiospecific Alkylation of Histidine and Histamine at N-1 (t)¹, Tetrahedron, vol. 52, No. 15, 1996, pp. 5363-5370.
Schibli et al., Influence of the denticity of ligand systems on the in vitro . . . , Bioconjugate Chemistry, 2000, pp. 345-351, vol. 11 No. 3.
Alberto et al., Synthesis and Properties of Boranocarbonate: A Convenient in situ . . . , J. Am. Chem. Soc., 2001, pp. 3135-3136, vol. 123.
La Bella et al., A '99m! Tc(I)-postlabelled high affinity bombesin analogue as a potential . . . , Bioconjugate Chemistry, 2002, pp. 599-604, vol. 13 No. 3.
Bullock et al., Characterization of novel histidine-tagged Tat-peptide complexes . . . , Bioconjugate Chemistry, 2002, pp. 1226-1237, vol. 13 No. 6.
Du et al., Technetium-99m Labelling of Glycosylated Somatostatin-14, Applied Radiation and Isotopes, 2001, pp. 181-187, vol. 55 No. 2.
Schibli et al., Current use and future potential of organometallic radiopharmaceuticals, 2002, pp. 1529-1542, vol. 29 No. 11.
Pak et al., N-epsilon Functionalization of Metal and Organic Protected L-histidine for a highly . . . , Chemistry European Journal, 2003, pp. 2053-2061, vol. 9.
Alberto et al., Synthesis and Reactivity of [NEt4]x[/re/br3(CO)3]. Formation and Structural . . . , J. Chem. Soc., Dalton Trans., 1994, p. 2815.
Jain et al., Regiospecific Alkylation of Histidine and Histamine at . . . , Tetrohedron, 1996, p. 5363, vol. 52 No. 15.

* cited by examiner

*Primary Examiner* — D L Jones

(57) ABSTRACT

The present invention relates to novel histidine derivates that can be used for the labeling of biomolecules with radioactive metal tricarbonyls. The new derivatives have a histidine that is derivatized at the $N^\epsilon$ and at least protected at the $N^\alpha$ and optionally at the $N^\delta$; or derivatized at the $N^\alpha$ and at least protected at the $N^\alpha$ and optionally at the $N^\delta$; or derivatized at the $N^\epsilon$ and $N^\alpha$ and at least protected at the $N^\alpha$ and optionally at the $N^\delta$; or derivatized at the $N^\epsilon$; or derivatized at the $N^\alpha$; or derivatized at the $N^\epsilon$ and $N^\alpha$; or at least protected at the $N^\alpha$ and optionally at the $N^\delta$.

7 Claims, 3 Drawing Sheets

N AND/OR $N^\alpha$ DERIVATIZED, METAL AND ORGANIC PROTECTED L-HISTIDINE FOR COUPLING TO BIOMOLECULES FOR HIGHLY EFFICIENT LABELING WITH $[M(OH_2)_3(CO)_3]^+$ BY FAC COORDINATION

CROSS-REFERENCE TO RELATED APPLICATION

This application claims the benefit of PCT/EP04/04683, filed Apr. 29, 2004, which claims the benefit of EP Application No. 2003076252.0 filed Apr. 29, 2003, both of which are incorporated herein in their entirety.

The invention relates to new histidine derivatives that can be coupled to biomolecules, such as amino acids, peptides etc. for labeling with a radioactive metal tricarbonyl $[M(OH_2)_3(CO)_3]^+$ by fac coordination.

The labeling of biologically active molecules with $^{99m}Tc$ for radiopharmaceutical purposes is a field of intense research. The commercially available perfusion agents for radioimaging have to be complemented by labeled vectors which will allow a more precise targeting of various receptors expressed in higher density on i.e. cancer cells. So far, a few compounds are in pre-clinical trials but none has found commercial application so far.

Many chemical and biological difficulties have to be overcome. Chemically, the targeting vector has to be i) derivatized with an appropriate chelator for $^{99m}Tc$ or other radionuclide, ii) should be labeled at high specific activity (low vector concentration) and finally retain its physico-chemical properties and its affinity towards the corresponding receptor. For routine use, the labeling process must be performed preferentially in one single step.

Different procedures are available from literature and for peptides in particular the hynic approach seems to be promising although it suffers from the lack of a clearly defined compound which is required for clinical approval.

The present inventors recently presented the one pot synthesis of the organometallic aqua-ion $[^{99m}Tc(OH_2)_3(CO)_3]^+$ (Alberto et al., J. Am. Chem. Soc. 2001, 123, 3135) and showed the versatility of using this complex fragment for the labeling of various biomolecules and peptides in particular.

One of the major advantages of the carbonyl approach is the availability of a well-defined complex with very high specific activity only depending from the ligand type. Naturally occurring bidentate ligands such as N-terminal histidines in peptide chains can efficiently be labeled with $[^{99m}Tc(OH_2)_3(CO)_3]^+$. An improvement in respect of specific activity was the introduction of a terminal histidine through the α-amino group which allowed labeling at low ligand concentration.

However, this type of bifunctional chelator has a relatively high lipophilicity and its synthesis is difficult.

It is therefore the object of the invention to provide a differently derivatized histidine which would allow its introduction into or onto any peptide with a minimum of synthetic work and a maximum of labeling efficiency.

The inventors contemplated that since the complex $[^{99m}Tc(his)(CO)_3]$ is hydrophilic it is appropriate to derivatize the histidine at the ε-nitrogen in the imidazole ring. This functionalization leaves the highly efficient tripodal coordination site untouched but still allows the coupling to amine or carboxylic groups in biomolecules. Finally, since the synthesis of $[^{99m}Tc(his)(CO)_3]$ can be performed in one single step from $[^{99m}TcO_4]^-$, histidine also fulfils the requirement for a one pot labeling procedure without affecting the ligand.

The invention thus relates to histidine derivatives, comprising a histidine that is any one of the following:

a) derivatized at the $N^\epsilon$ and at least protected at the $N^\alpha$ and optionally at the $N^\delta$; or
b) derivatized at the $N^\alpha$ and at least protected at the $N^\alpha$ and optionally at the $N^\delta$; or
c) derivatized at the $N^\epsilon$ and $N^\alpha$ and at least protected at the $N^\alpha$ and optionally at the $N^\delta$; or
d) derivatized at the $N^\epsilon$; or
e) derivatized at the $N^\alpha$; or
f) derivatized at the $N^\epsilon$ and $N^\alpha$; or
g) at least protected at the $N^\alpha$ and optionally at the $N^\delta$.

The $N^\epsilon$ and/or $N^\alpha$ are derivatized with $-(CH_2)_n-R$ wherein n=0, 1, 2, 3, 4, 5, 6, 7, 8, 9 or 10, preferably 1, 2, 3, 4 or 5, and R is a group selected from $-NH_2$, $-COOR_1$, $-OH$, $-X$ or $-X'$-biomolecule, wherein X' is a coupling block having a bond that is the result from a reaction between COOH and $NH_2$, $NH_2$ and COOH, OH and Ph-OH, wherein Ph is phosphoric acid group on the biomolecules, such as phosphorylated peptide or glycosyl phosphates or X and an electrophilic functional group on the biomolecule, in particular S, OH or amine and $R_1$ is H, t-butyl or pentafluorophenyl. X is suitably selected from halides, azides, pseudohalides, phosphate, thiol, silyl.

Either or both of $N^\epsilon$ and $N^\alpha$ can be derivatized with a biomolecule. This can be any biomolecule, in particular polypeptides, such as antibodies, peptides, amino acids, sugars, vitamins. Suitable examples of biomolecules are bombesine, (alpha)-MSH peptides, such as melanocortin, octreotate, somatostatin, interleukin-8 (IL8), CCK, (beta)-hairpin loop peptides, neurotensin, biotin, monoclonal antibodies, such as monoclonal antibodies directed against prostate membrane specific antigen (pmsa).

The biomolecule can be coupled directly to the $N^\epsilon$ and/or $N^\alpha$ or the $N^\epsilon$ and/or $N^\alpha$ can be first derivatized with a group of the formula $-(CH_2)_n-R$, wherein R is as defined above.

The $N^\alpha$ and $N^\delta$ can be protected with a carbonyl thus forming a six-membered urea ring. Alternatively, $N^\alpha$, $N^\delta$ and the carboxyl group are protected with a metal tricarbonyl.

These two forms of protection are in particular useful when derivatization with $-(CH_2)_n-R$ is to take place. When subsequently this group is further derivatized with a biomolecule the original protection may be replaced by protection of $N^\alpha$ with a amine protecting group, in particular Fmoc, Cbz, BOC, Teoc, methoxycarbonyl, ethoxycarbonyl, and protection of the carboxyl group by esterification.

After all derivatization steps are completed the histidine derivative can be deprotected and subsequently coordinated to a radioactively labeled metal tricarbonyl to obtain a labeled biomolecule.

The radioactively labeled metal tricarbonyl is suitably selected from $[^{99m}Tc(OH_2)_3(CO)_3]^+$, $[^{188}Re(OH_2)_3(CO)_3]^+$ and $[^{97}Ru(OH_2)_3(CO)_3]^{2+}$.

According to a further aspect of the invention it was found that coupling of the biomolecule is highly facilitated when the $-(CH_2)_n-R$ on $N^\epsilon$ is derivatized as $-(CH_2)_n-COO$-pentafluorophenyl ester. This derivatization leads to an activation of the COOH on $N^\epsilon$, which gives a possibility of direct conjugation with biomolecules without any modification when a biomolecules itself has free carboxylic acid that might be competitive for coupling. In the above situation $N^\alpha$ and the carboxylic part are protected.

The present invention relates in particular to histidine derivatives having one of the following structural formulas

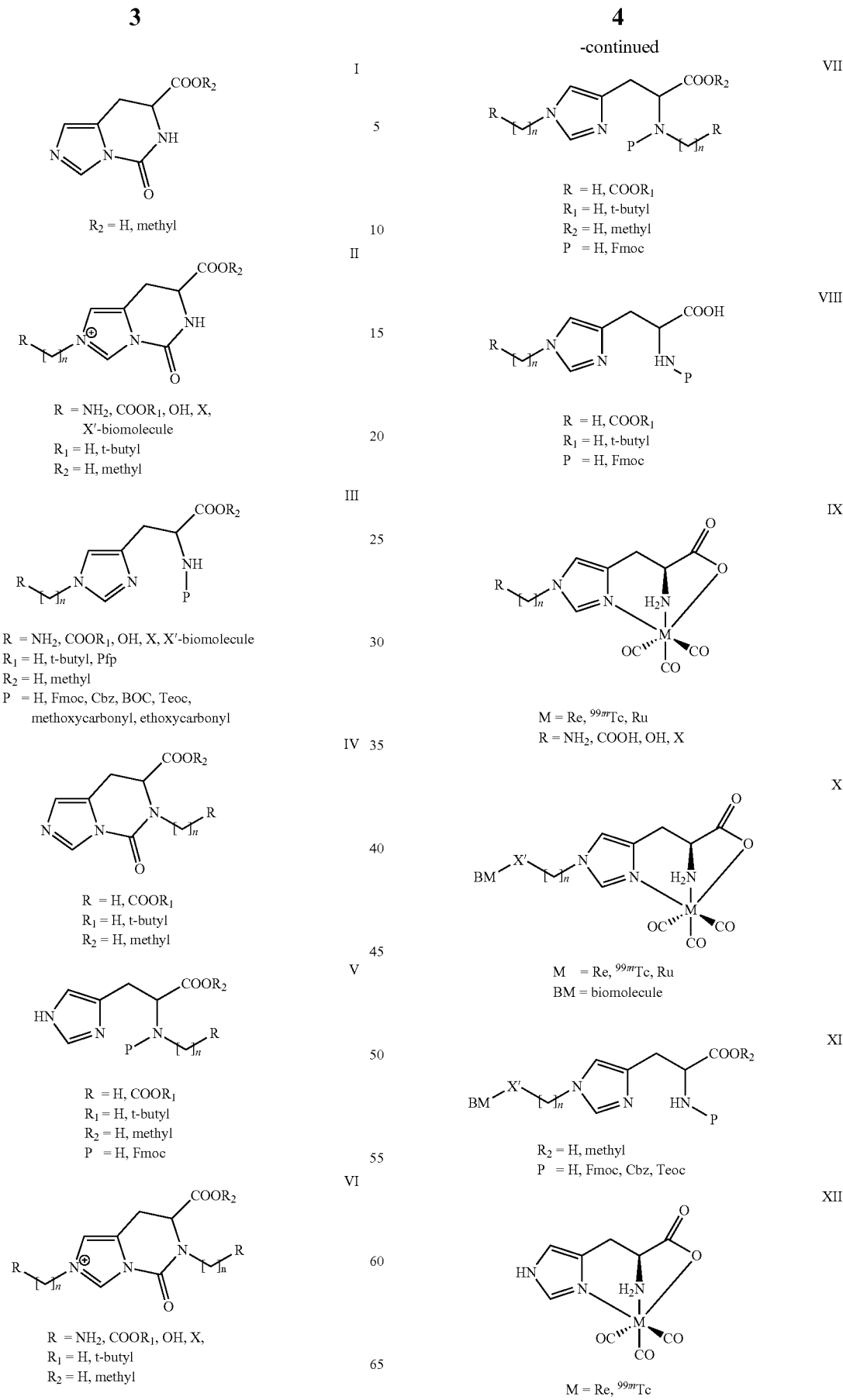

-continued

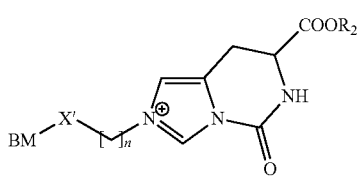

XIII $R_2$ = H, methyl
BM = biomolecule

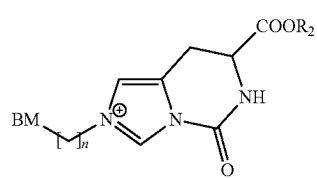

XIV $R_2$ = H, methyl
BM = biomolecule

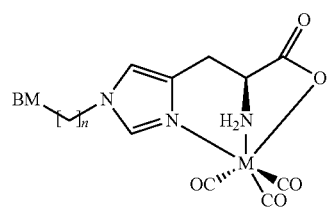

XV

M = Re, $^{99m}$Tc, Ru
BM = biomolecule

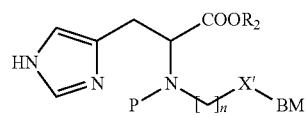

XVI $R_2$ = H, methyl
P = H, Fmoc
BM = biomolecule

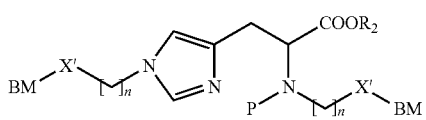

XVII $R_2$ = H, methyl
P = H, Fmoc
BM = biomolecule

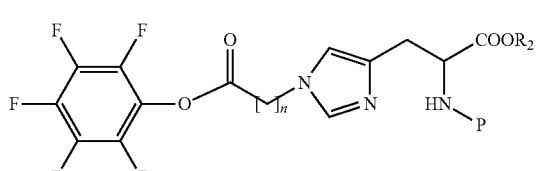

XVIII $R_2$ = H, methyl
P = H, Fmoc

According to a further aspect thereof, the invention relates to biomolecules coupled to a histidine derivative as claimed.

The histidine can be at the end or within the biomolecule. Alternatively, both $N^\epsilon$ and $N^\alpha$ can be derivatized with a biomolecule leading to dimers or to bifunctional molecules. Examples of bifunctional molecules are molecules in which one side of the biomolecule has a targeting function, such as an antibody or a ligand to a receptor and the other side of biomolecule is used for its toxicity. Other combinations are also part of this invention. Such bifunctional molecules can for example be used for the targeted treatment of tumors. The targeting to a tumor will bring the toxic biomolecule and the radioactive metal in the vicinity of the tumor to be treated.

Suitable biomolecules are bombesine, (alpha)-MSH peptides, such as melanocortin, octreotate, somatostatin, interleukin-8 (IL8), CCK, (beta)-hairpin loop peptides, neurotensin, biotin, monoclonal antibodies, such as monoclonal antibodies directed against prostate membrane specific antigen (pmsa).

In the research that led to the invention two different pathways were found for the introduction of an acetyl group at $N^\epsilon$ in $N^\alpha$, $N^\delta$ and —COO protected histidine to afford the model compound $N^\epsilon$—(CH$_2$COOH)-histidine derivative 9. Compounds of the invention, like histidine derivative 9, can be coupled to amino groups in bioactive molecules such as peptides. After full deprotection of such a bioconjugate, histidine provides three coordination sites which efficiently coordinate to $[^{99m}Tc(OH_2)_3(CO)_3]^+$ or $[Re(OH_2)_3(CO)_3]^+$ $[^{97}Ru(OH_2)_3(CO)_3]^{2+}$ in a facial geometry.

The invention thus also provides a method for preparing histidine derivatives of the invention, comprising:

a) providing histidine;

b) protecting at least the $N^\alpha$ and optionally the carboxyl and the $N^\delta$;

c) derivatizing at least one of the $N^\epsilon$ and $N^\alpha$; and d) deprotecting the protected groups.

The method may further comprise the step e) of labeling the deprotected compound to obtain a labeled compound.

In the method the $N^\alpha$ and $N^\delta$ may be protected by a carbonyl group thus forming a six-membered urea ring or the carboxyl, $N^\alpha$ and $N^\delta$ may be coordinated to a metal, in particular a metal tricarbonyl.

The derivatization of $N^\epsilon$ and/or $N^\alpha$ can be performed with —(CH$_2$)$_n$—R wherein n=0, 1, 2, 3, 4, 5, 6, 7, 8, 9 or 10, preferably 1, 2, 3, 4 or 5, and R is a group selected from —NH$_2$, —COOR$_1$, —OH, —X or —X'-biomolecule, wherein X' is a coupling block having a bond that is the result from a reaction between COOH and NH$_2$, NH$_2$ and COOH, OH and Ph-OH, wherein Ph is phosphoric acid group on the biomolecules, such as phosphorylated peptide or glycosyl phosphates or X and an electrophilic functional group on the biomolecule, in particular S, OH or amine, wherein R$_1$ is H, t-butyl. Alternatively, $N^\epsilon$ and/or $N^\alpha$ can be directly derivatized with a biomolecule.

When protection is achieved by means of the urea ring and derivatization of —(CH$_2$)$_n$—R takes place at $N^a$, the ring may be opened prior to introducing the biomolecule. In that case the carboxyl is protected by esterification and the $N^\alpha$ is protected with an amine protecting group, such as Fmoc, Cbz, BOC, Teoc, methyloxycarbonyl, or ethyloxycarbonyl group.

In order to facilitate derivatization, —(CH$_2$)$_n$—R on $N^\epsilon$ may first be derivatized as —(CH$_2$)$_n$—COO-pentafluorophenyl ester.

When the method comprises the step of labeling the derivative this is suitably done with a radioactively labeled metal tricarbonyl, in particular a radioactively labeled metal tricarbonyl selected from $[^{99m}Tc(OH_2)_3(CO)_3]^+$, $[^{188}Re(OH_2)_3(CO)_3]^+$ and $[^{97}Ru(OH_2)_3(CO)_3]^{2+}$.

Selective derivatization at the $N^\epsilon$ position has thus conveniently been achieved by concomitant protection of $N^\alpha$ and $N^\delta$ with a carbonyl group forming a six-membered urea. Cyclic urea ring opening with Fm—OH, coupling of phenyl-alanine as a model to 9 through its primary amine and removal of all protecting groups in one step gave a histidine derivative of phenyl-alanine which could be labeled at $10^{-5}$ M with $^{99m}Tc$ in very high yield and even in about 50% yield at $10^{-6}$M. The x-ray structure of a complex with $[Re(CO)_3]^+$ in which anilin is coupled to 9 confirms the facial arrangement of histidine.

A second pathway applies directly the $[Re(CO)_3]^+$ moiety as a protecting group as shown in the scheme below.

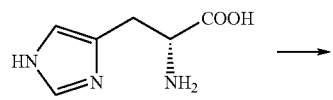

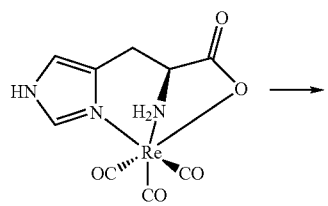

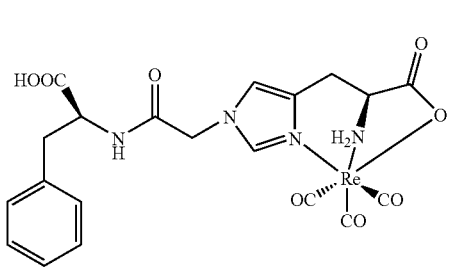

This is one of the rare examples in which a metal fragment is used as a protecting group for organic functionalities.

The coordination to histidine protects $N^\alpha$, $N^\delta$ and —COO in one single step, subsequent alkylation with $BrCH_2COOH$ (R) at $N^\epsilon$, coupling to phenyl-alanine and oxidative deprotection of $[Re(CO)_3]^+$ to $[ReO_4]^-$ gave the corresponding bioconjugate in which histidine is coupled to phenyl-alanine through an acetylamide at $N^\epsilon$.

Both methods offer convenient pathways to introduce histidine in a biomolecule under retention of its three coordination sites. The procedures are adaptable to any biomolecule with pendant amines and allow the development of novel radiopharmaceuticals or inversed peptides.

Thus, a high yield labeling of biomolecules with $[^{99m}Tc(OH_2)_3(CO)_3]^+$ is possible at µM concentrations, when histidine is linked through $N^\epsilon$ in the imidazole ring to a targeting molecule. Two convenient strategies to produce such derivatives have been worked out, one employing the $[Re(CO)_3]^+$ core as an organometallic protecting group for three functionalities in histidine. The key compounds can be coupled to any amino group in a biomolecule and be labeled in one single step from $[^{99m}TcO_4]^-$ in water which enables the development of new radiopharmaceuticals.

The derivatization method of choice depends on the biomolecule to be coupled. The opening of the urea ring requires acidic pH and reducing conditions but is generally performed prior to biomolecule coupling. This method is suitable for biomolecules that can withstand such conditions, such as vitamins. Alternatively, polypeptides can be coupled to a histidine that is protected with the metal carbonyl.

Below examples are listed of various types of histidine derivatives for highly efficient and biologically stable labeling of biomolecules.

$N^\alpha$ and $N^\delta$ can be protected in one single step, leaving $N^\epsilon$ free for further derivatizations. Derivatizations at $N^\alpha$ are possible as well.

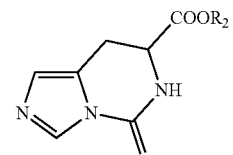

$R_2$ = H, methyl

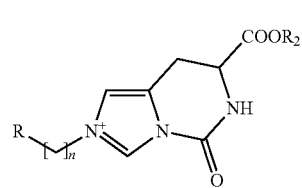

(Molecule 1)

R = $NH_2$, $COOR_1$, OH, X
$R_1$ = H, t-butyl
$R_2$ = H, methyl

The left molecule shows the histidine in which $N^\alpha$ and $N^\delta$ are protected and $N^\epsilon$ is left for derivatization, which is shown in the right hand molecule. Derivatization (such as alkylation) at $N^\epsilon$ leads to a variety of derivatives that can be coupled to biomolecules through the pendant functionality, which can be an amine, a carboxylate, a halide and others. This kind of synthesis is essentially literature known (R. Jain, et al, J. Chem. Soc., Dalton Trans, 1994, 2815). After deprotection, a histidine derivative with possibility of tripodal coordination via the $N^\alpha$, to $[M(CO)_3]^+$ remains:

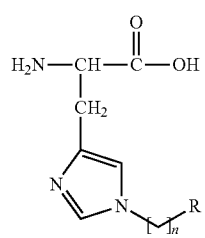

R = $NH_2$, $COOR_1$, OH, X
$R_1$ = H, Pentafluorophenol

Before deprotection, molecule 1 can be coupled to a biomolecule of any kind. R can thus also be a biomolecule. Deprotection yields then again a biomolecule that contains a tripodal histidine ligand. This ligand is of highest efficiency in terms of labeling with $^{99m}Tc$ or $^{188}Re$ and allows the labeling of biomolecules almost on the n.c.a. level.

The following is an example of tripodal histidine coupled to a model peptide sequence:

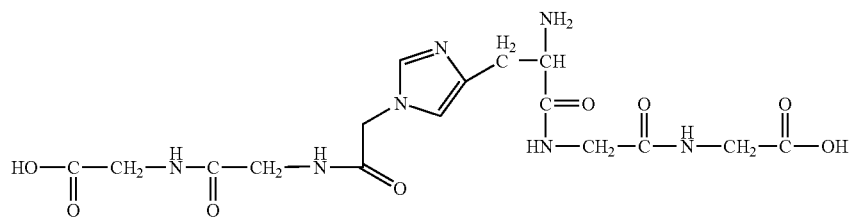

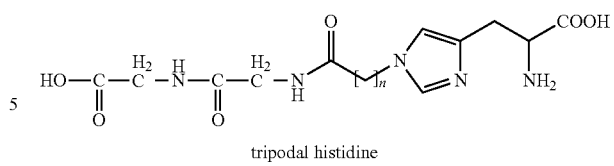

tripodal histidine

The combination of synthetic techniques and biomolecule labeling is novel and the high yields unexpected. Moreover, according to the invention the very powerful carbonyl ligand can now be coupled to a biomolecule very easily. Derivatives of the above mentioned type can be coupled to essentially any biomolecule under retention of its physico-chemical properties. Histidine coupled in the way according to the invention is a natural ligand.

Furthermore, histidine derivatives of the invention can be used to reverse the direction of a peptide chain. A normal peptide sequence has for example the following structural formula:

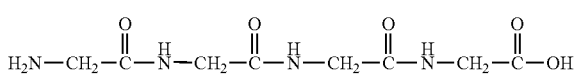

By means of the histidine derivatives of the invention reversed sequences can be produced to yield two N-termini and a bidentate his ligand:

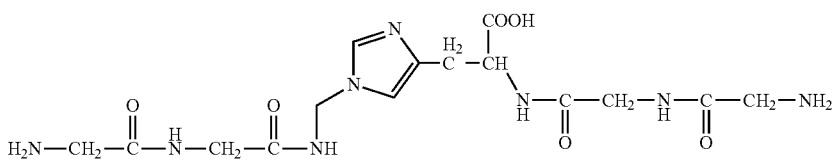 [SMILES: NCC(=O)NCC(=O)NCn1cnc(CC(NC(=O)CNC(=O)CN)C(=O)O)c1]

Alternatively a reversed sequence with two C-termini and a bidentate his ligand can be obtained:

Histidine derivatives can also be involved in the peptide chain without reversing the sequence, such as in the following normal sequence with a bidentate histidine ligand in the sequence:

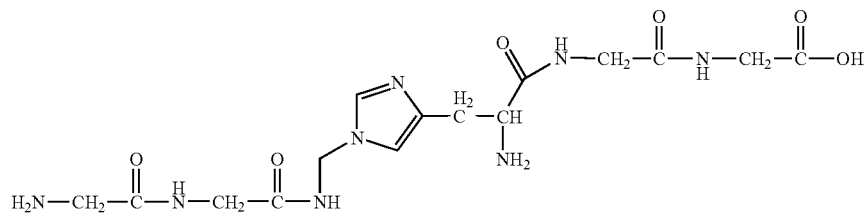 [SMILES: NCC(=O)NCC(=O)NCn1cnc(CC(N)C(=O)NCC(=O)NCC(=O)O)c1]

In this case it is possible to include a bidentate, natural ligand in a normal peptide sequence. This inclusion in the peptide chain yields a novel kind of labeling which has not been realized so far.

Modification at $N^\alpha$ in structure yields a semi-natural histidine. Derivatization at either $N^\alpha$ or $N^\epsilon$ is selectively possible as follows:

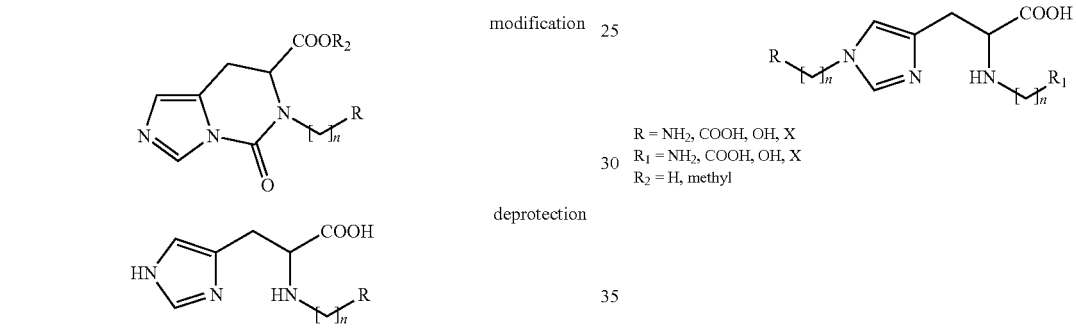

$R = NH_2, COOR_1, OH, X$
$R_1 = H$, t-butyl
$R_2 = H$, methyl $R = NH_2, COOH, OH, X$
$R_1 = NH_2, COOH, OH, X$
$R_2 = H$, methyl Alternatively, coupling of peptide sequences in either R or $R_1$ allows the inclusion of tridentate histidine in a peptide sequence which can be normal (bottom) or reversed (top).

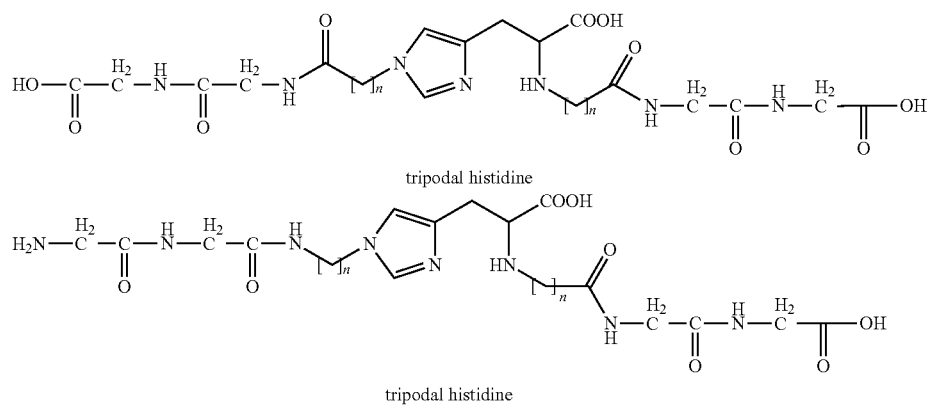

Derivatization at both $N^\alpha$ and $N^\epsilon$ is possible at the same time, introducing different functionalities (including also biomolecules) (left) to yield a trifunctional histidine after deprotection, which then gives a trifunctionalized tripodal histidine ligand (right):

Both strategies allow also the labeling of small molecules by applying the highly efficient and strong histidine ligand. This can be used for i.e. the labeling of amino acids or other small molecules such as hypoxia imaging agents. The [Tc(his-R) (CO)$_3$] complex is thereby of high hydrophilicity which is in general an advantage for biological molecules.

It should be noted that in this application the compounds as depicted in structural formulas I to XVIII are generalized structures. The following Table 1 summarizes the combination of features for each general formula.

TABLE 1

|   | A | B | C | D |
|---|---|---|---|---|
| 1 | II/XIII | IX/X | III/XI XVIII/XI | III, XI |
| 2 | IV/— | np/np | V/XVI | V, XVI |
| 3 | VI/— | np/np | VII/XVII | VII, XVII |
| 4 | I/XIV | XII/XV | — | histidine |

1 = derivatized at $N^\epsilon$
2 = derivatized at $N^\alpha$
3 = derivatized at $N^\epsilon$ and $N^\alpha$
4 = not derivatized
A = protected by means of six-membered ring
B = protected by means of metal tricarbonyl
C = protected by ester on COOH and amine protecting group on $N^\alpha$
D = formula with deprotected COOH and $N^\alpha$ *from column C for labeling*
bold = formula without biomolecule
*italic* = formula with biomolecule
np = not possible It is the applicant's intention to disclose herein all possible combinations of the alkyl chain length expressed in the value of n and the various substituents R on $N^\alpha$ and/or $N^\epsilon$. The following is Table 2 in which all possible combinations of n and R are listed. In some of the compounds any one combination of two of the combinations listed below are possible.

TABLE 2

|   | 0 | 1 | 2 | 3 | 4 | 5 | 6 | 7 | 8 | 9 | 10 |
|---|---|---|---|---|---|---|---|---|---|---|---|
| $NH_2$ | 0/$NH_2$ | 1/$NH_2$ | 2/$NH_2$ | 3/$NH_2$ | 4/$NH_2$ | 5/$NH_2$ | 6/$NH_2$ | 7/$NH_2$ | 8/$NH_2$ | 9/$NH_2$ | 10/$NH_2$ |
| COOH | 0/COOH | 1/COOH | 2/COOH | 3/COOH | 4/COOH | 5/COOH | 6/COOH | 7/COOH | 8/COOH | 9/COOH | 10/COOH |
| OH | 0/OH | 1/OH | 2/OH | 3/OH | 4/OH | 5/OH | 6/OH | 7/OH | 8/OH | 9/OH | 10/OH |
| X | 0/X | 1/X | 2/X | 3/X | 4/X | 5/X | 6/X | 7/X | 8/X | 9/X | 10/X |

When the biomolecule is not coupled directly to the histidine but when the $N^\epsilon$ and/or $N^\alpha$ are derivatized first, the following combinations with n and R are possible.

TABLE 3

|   | 0 | 1 | 2 | 3 | 4 | 5 | 6 | 7 | 8 | 9 | 10 |
|---|---|---|---|---|---|---|---|---|---|---|---|
| $NH_2$ | 0/NH-BM | 1/NH-BM | 2/NH-BM | 3/NH-BM | 4/NH-BM | 5/NH-BM | 6/NH-BM | 7/NH-BM | 8/NH-BM | 9/NH-BM | 10/NH-BM |
| COOH | 0/CO-BM | 1/CO-BM | 2/CO-BM | 3/CO-BM | 4/CO-BM | 5/CO-BM | 6/CO-BM | 7/CO-BM | 8/CO-BM | 9/CO-BM | 10/CO-BM |
| OH | 0/O-BM | 1/O-BM | 2/O-BM | 3/O-BM | 4/O-BM | 5/O-BM | 6/O-BM | 7/O-BM | 8/O-BM | 9/O-BM | 10/O-BM |
| X | 0/X'-BM | 1/X'-BM | 2/X'-BM | 3/X'-BM | 4/X'-BM | 5/X'-BM | 6/X'-BM | 7/X'-BM | 8/X'-BM | 9/X'-BM | 10/X'-BM |

NH—BM means that the $NH_2$ on the $N^\epsilon$ and/or $N^\alpha$ of the histidine derivative is coupled to the COOH of the biomolecule. In CO—BM the COOH on the $N^\epsilon$ and/or $N^\alpha$ of the histidine derivative is coupled to the $NH_2$ of the biomolecule. O—BM means that the OH on the $N^\epsilon$ and/or $N^\alpha$ of the histidine derivative is coupled to the Ph-OH or halide on the biomolecules by the formation of a phosphate-ester or an ether linking group of the biomolecule. And X'—BM means that the halide, azide, pseudohalide, phosphate, thiol or silyl on the $N^\epsilon$ and/or $N^\alpha$ of the histidine derivative is coupled to S, OH or amine on the biomolecule.

The invention will be further illustrated in the Examples that follows and that is not intended to limit the invention in any way. The Examples describe a model system for the labeling of biomolecules. It should be noted that in the same manner other biomolecules, such as amino acids and peptides can be labeled. In the Example reference is made to the following figures:

EXAMPLES

Example 1

Figure 1:
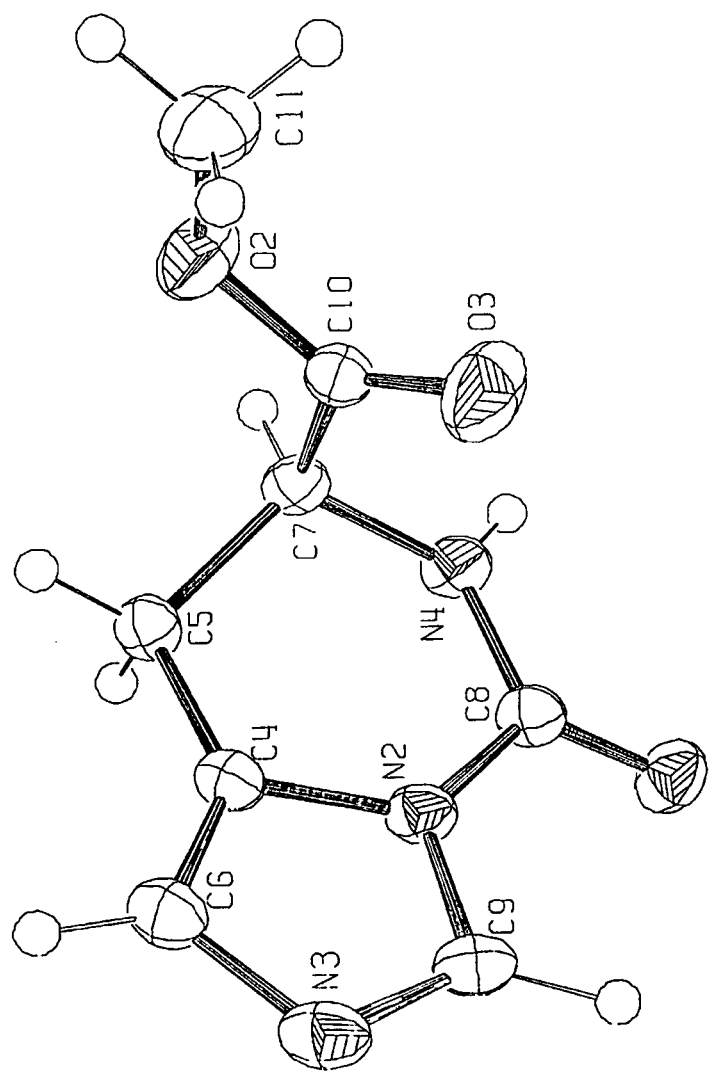
FIG. 1: Ortep plot of 3, ellipsoids drawn at 50% probability.
Figure 2:
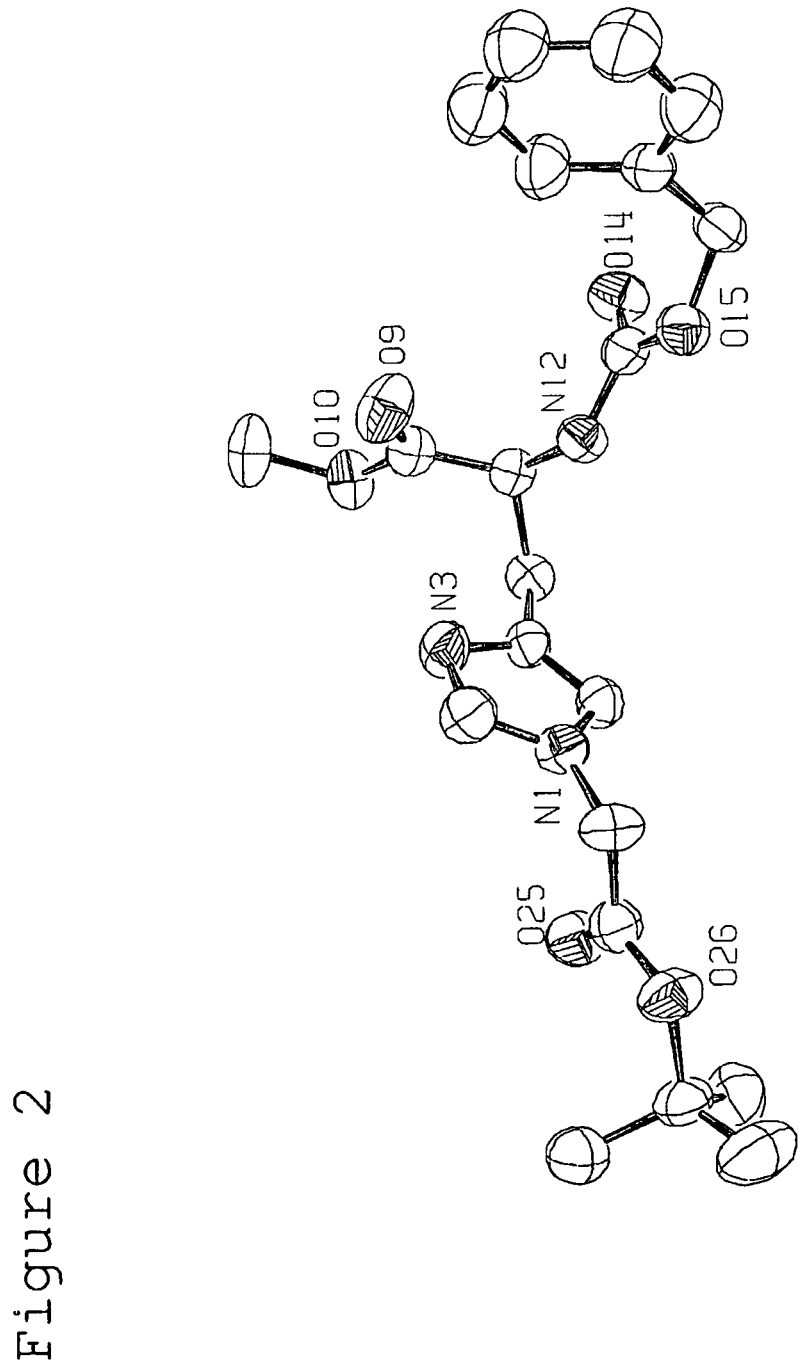
FIG. 2: Ortep plot of 6, ellipsoids drawn at 50% probability, showing one of the two molecules in the asymmetric unit.
Figure 3:
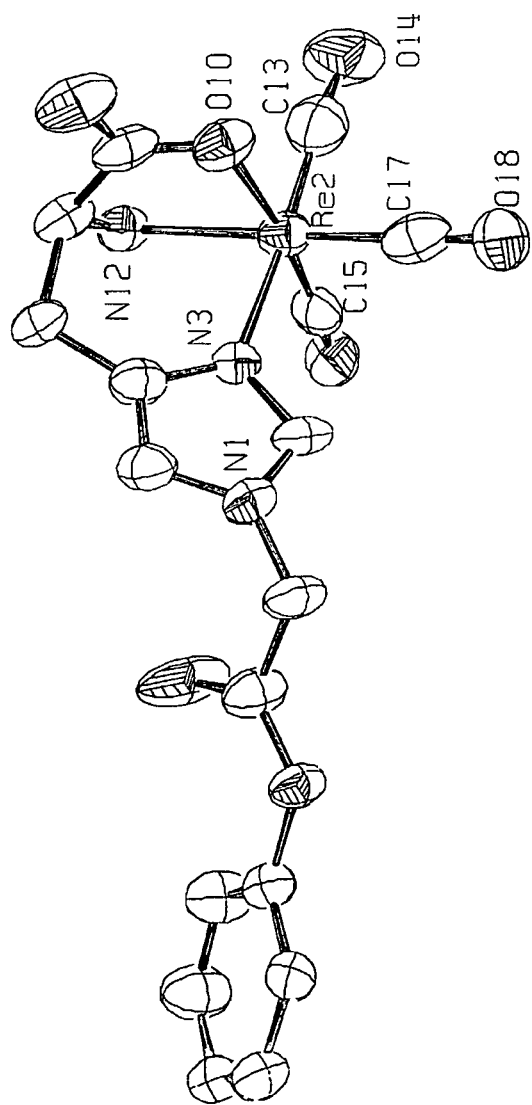
FIG. 3: Ortep plot of 13, ellipsoids drawn at 50% probability, showing one of the two molecules in the asymmetric unit.

Synthesis of $N^\alpha$ and $N^\delta$ Protected Urea-Histidine (Scheme 1)

5-Oxo-5,6,7,8-tetrahydroimidazo[1,5-c]pyrimidine-7-carboxylic acid methyl ester (molecule 3)

The compound was prepared according to literature with slight modification. (R. Jain et al. Tetrahedron, 1996, 52, 5363) To a solution of L-histidine methylester (2.73 g, 11.28 mmol) in DMF (80 ml) was added $Im_2CO$ (1.88 g, 11.61 mmol) at r.t. The reaction mixture was heated to 70° C. for 6 h, cooled down to r.t. and poured slowly to 1M $NaHCO_3$ aqueous solution (250 ml). Some solid precipitated from the water layer, which was extracted with $CH_2Cl_2$. During extraction the precipitate dissolved completely in $CH_2Cl_2$.

The combined organic extracts were dried over $Na_2SO_4$, concentrated under reduced pressure, and purified by flash column chromatography to afford 3 as white solid (1.35 g, 61%). $R_f$=0.2 (EtOAc 100%); $^1$H NMR (500 MHz, $CD_3CN$, 25° C.): δ=8.01 (s, 1H; $CH_{im}$), 6.77 (s, 1H; $CH_{im}$), 6.61 (br.s, 1H; NH), 4.37-4.34 (m, 1H; CHCO), 3.67 (s, 3H; $OCH_3$), 3.25-3.23 (m, 2H; $CH_2CH$); $^{13}$C NMR (500 MHz, $CD_3CN$, 25° C.): δ=172.1, 149.2, 135.4, 126.9, 125.9, 53.6, 53.5, 23.7;

MS (ESI): m/z(%): 195.73 (100) [M+], 167.8 (35), 135.8 (24); elemental analysis calcd (%) for $C_8H_9N_3O_3$ (195.18): C, 49.23; H, 4.62; N, 21.54; found: C, 49.32; H, 4.77; N, 21.24.

Crystals suitable for x-ray structure analysis were obtained by slow evaporation from EtOAc.

Example 2

Introduction of Carboxylate Functionality in $N^\epsilon$ (Scheme 1)

2-(2-tert-Butoxy-2-oxoethyl)-7-methoxycarbonyl-5-oxo-5,6,7,8-tetrahydroimidazo[1,5-c]pyrimidine-2-ium; bromide (molecule 4)

Bromoacetic acid tert-butyl ester (0.57 ml, 3.86 mmol) was added to a solution of 3 (250 mg, 1.28 mmol) in $CH_3CN$ (25 ml). The reaction mixture was refluxed for 24 h, cooled to r.t. and concentrated in vacuo. The residue was washed with $Et_2O$ (2×10 ml) and THF (2×5 ml) and dried in vacuo to afford 4 as a white sticky solid, which was used in the next step without any further purification. $^1$H NMR (300 MHz, $D_2O$, 20° C.): δ=9.39 (s, 1H; $CH_{im}$), 7.40 (s, 1H; $CH_{im}$), 5.05 (s, 2H; $CH_2N_{im}$), 4.78-4.61 (m, 1H; CHCO), 3.63 (s, 3H; $OCH_3$), 3.42-3.39 (m, 2H; $CH_2CH$), 1.39 (s, 9H; tBu); MS (ESI): m/z (%): 309.40 (13) [M+−HBr], 253.80 (100) [M+−HBr−($CH_2$=$C(CH_3)_2$)].

Example 3

Preparation of $N^\epsilon$ Protected Histidine (Scheme 1)

Methyl N-[(benzyloxy)carbonyl]-1-(2-tert-butoxy-2-oxoethyl) histidinate (molecule 6)

To a solution of crude 4 (390 mg) in THF (50 ml) were added DIPEA (0.52 ml, 3.01 mmol) and BnOH (2.1 ml, 20.08 mmol). After 16 h of refluxing, the reaction solution was cooled down to room temperature, concentrated under reduced pressure, and purified by flash column chromatography to afford 6 as white solid (260 mg, 62% from 3). $R_f$=0.15 ($CH_2Cl_2$/MeOH 45:1); $^1$H NMR (500 MHz, $CD_3CN$, 25° C.): δ=7.39-7.32 (m, 6H; 5×$CH_{ph}$, $CH_{im}$), 6.78 (s, 1H; $CH_{im}$), 6.66 (br.d, J=7.8 Hz, 1H; NH), 5.06 (s, 2H; $CH_2$—Bn), 4.58 (s, 2H; $CH_2N_{im}$), 4.42 (q, J=2.6 Hz, 1H; CHCO), 3.62 (s, 3H; $OCH_3$), 2.96 (t, J=5.26 Hz, 2H; $CH_2CH$); $^{13}$C NMR (500 MHz, $CD_3CN$, 25° C.): δ=173.2, 168.3, 157.0, 139.1, 138.2, 137.8, 129.5, 129.0, 128.9, 119.2, 83.2, 67.2, 66.9, 55.2, 52.7, 49.3, 30.2, 28.2; MS (ESI): m/z (%): 417.53 (100) [M+]; elemental analysis calculated (%) for $C_{21}H_{27}N_3O_6$ (417.48): C, 60.43; H, 6.47; N, 10.07; found: C, 60.43; H, 6.57; N, 9.97.

Crystals suitable for x-ray structure analysis were obtained by vapor diffusion of 1-hexene into EtOAc.

Example 4

Preparation of a Histidine Compound with Deprotected Functionality and Coupling to a Biomolecule (Scheme 2)

Methyl N-[(benzyloxy)carbonyl]-1-{2-[(1-ethoxy-carbonyl-2-phenylethyl)amino]-2-oxoethyl} histidinate (molecule 10a)

A solution of 6 (140 mg, 0.34 mmol) in $CH_2Cl_2$/TFA (2:2 ml) was stirred for 2.5 h at r.t. The solvent was removed under reduced pressure and dried more in vacuo. The residue, the crude compound 8 was dissolved in $CH_2Cl_2$ (10 ml) and neutralized by adding $Et_3N$ dropwise. BOP (148 mg, 0.34 mmol) and $Et_3N$ (46 μl, 0.34 mmol) were added to the reaction mixture. After 45 min, a solution of phenylalanine-ethyl ester (84.6 mg, 0.37 mmol) and $Et_3N$ (51 μl, 0.37 mmol) in $CH_2Cl_2$ (10 ml) was added slowly by a syringe. The reaction mixture was stirred for 2.5 d more at room temperature. The solution was diluted with $CH_2Cl_2$ (30 ml) and extracted with 1N HCl solution (20 ml), 1N $NaHCO_3$ (20 ml), brine (20 ml). The organic layer was dried over $Na_2SO_4$, concentrated under reduced pressure and purified by flash column chromatography to afford 10a as colorless oil (162 mg, 90%). $R_f$=0.2 ($CH_2Cl_2$/MeOH 40:1); $^1$H NMR (500 MHz, $CD_3CN$, 25° C.): δ=7.37-7.28 (m, 9H; 2×4H—$CH_{ph}$, $CH_{im}$), 7.16 (d, J=8.23 Hz, 2H; 2×$CH_{ph}$), 6.77 (br.d, J=7.65 Hz, 1H; NH), 6.69-6.66 (m, 2H; $CH_{im}$, NH), 5.05 (s, 2H; $CH_2$—Bn), 4.61 (dt, J=7.86 Hz, 1H; CH-Phe), 4.52 (s, 2H; $CH_2N_{im}$), 4.43-4.41 (m, 1H; CHCO), 4.11 (q, J=7.15 Hz, 2H; $CH_2CH_3$), 3.62 (s, 3H; $OCH_3$), 3.10 (dd, J=8.19 Hz, 1H; $CH_2$-Phe), 2.99-2.93 (m, 3H; $CH_2$-Phe, $CH_2CH$), 2.57 (s, N—$CH_3$), 1.18 (t, J=7.13 Hz, 3H; $CH_3$); $^{13}$C NMR (500 MHz, $CD_3CN$, 25° C.): δ=173.3, 172.0, 167.8, 157.0, 139.1, 138.3, 138.2, 137.8, 130.4, 129.5, 129.4, 129.0, 128.9, 127.9, 118.9, 67.2, 62.2, 55.2, 54.8, 52.8, 49.9, 38.0, 30.3, 14.5; MS (ESI): m/z (%): 537.53 (100) [M++H]; elemental analysis calcd (%) for $C_{28}H_{32}N_4O_7$+0.5 [$N(CH_3)_2$]$_3$P=O+0.5$H_2O$ (634.5): C, 58.63; H, 6.62; N, 12.14; found: C, 58.98; H, 6.89; N, 12.48.

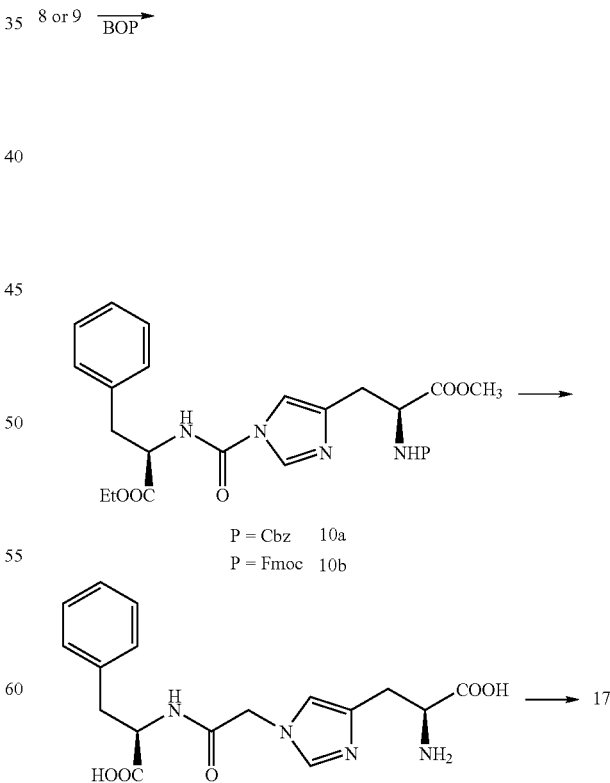

Scheme 2

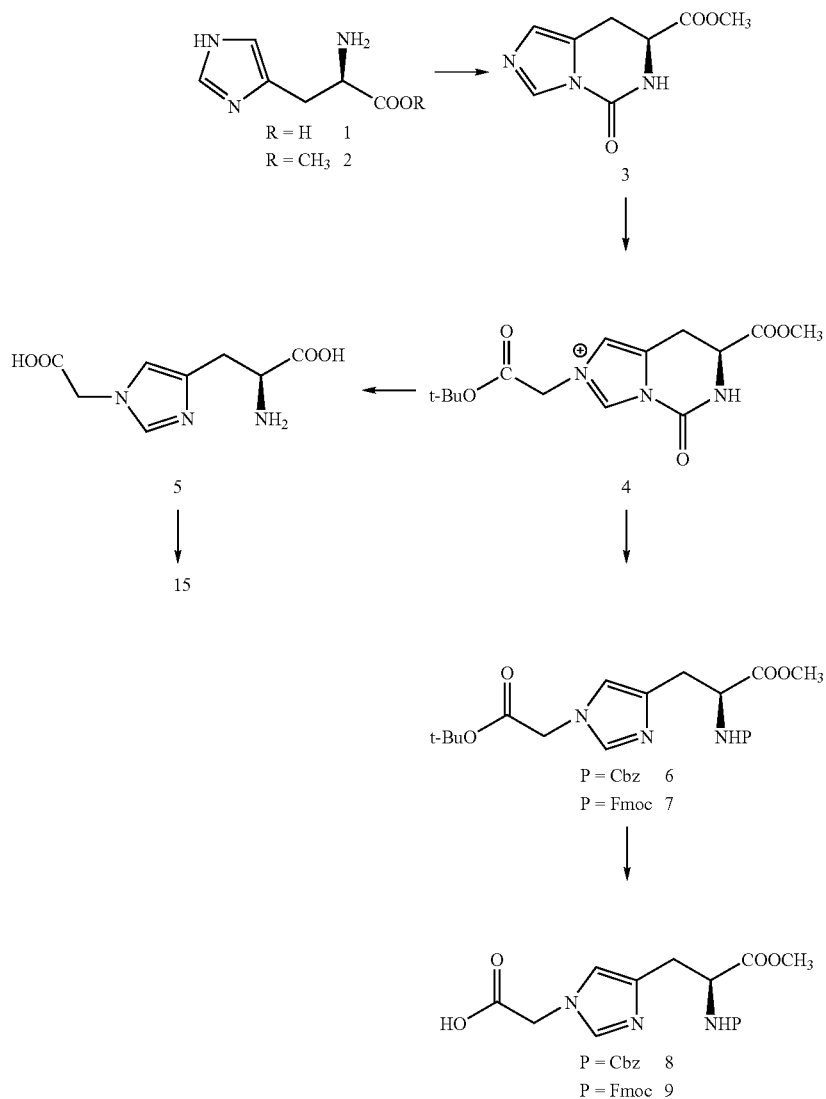

Scheme 1

Example 5

Introduction of a Functional Group at $N^\epsilon$ in $[Re(CO)_3]^+$ Protected Histidine (Scheme 3)

Re Complex (16a)

To a solution of complex 14, (25 mg, 0.059 mmol) and $Cs_2CO_3$ (20.4 mg, 0.065 mmol) in acetonitrile (25 ml) ethyl bromoacetate (29.5 mg, 0.176 mmol) in acetonitrile (5 ml) was added. The reaction mixture was heated at 35° C. for 1.5 h. Glacial acidic acid was added to the mixture to neutralize. After standard work-up, the crude substance was purified by a silica gel chromatography to provide complex 16a (30 mg, 90%). $R_f$=0.15 (EtOAc/EtOH 5:1); $^1$H NMR (300 MHz, $CD_3CN$, 20° C.): δ=7.95 (s, 1H; $CH_{im}$), 6.92 (s, 1H; $CH_{im}$), 4.78 (s, 2H; $CH_2N_{im}$), 4.23-4.16 (q, J=7.1 Hz, 2H; $CH_2CH_3$), 3.91-3.87 (m, 1H; CHCO), 3.21-2.98 (q, 2H; $CH_2CH$), 1.28-1.23 (t, J=7.5 Hz, 3H; $CH_3$); $^{13}$C NMR (300 MHz, $CD_3CN$, 20° C.): δ=199.5, 197.8, 197.8, 181.8, 168.8, 143.4, 135.7, 120.9, 63.0, 52.6, 49.4, 28.7, 14.4; MS (ESI): m/z (%): 511.8 (100) [M$^+$+H], 1020.7 (55) [2M$^+$]; elemental analysis calcd (%) for $C_{15}H_{18}N_3O_7Re$ (510.5): C, 30.59; H, 2.76; N, 8.23; found: C, 30.84; H, 3.0; N, 8.06.

Re Complex (16b)

The preparation is similar to compound 16a. To compound 14, (25 mg, 0.059 mmol) and $Cs_2CO_3$ (20.4 mg, 0.065 mmol) in acetonitrile (25 ml) was added tert-butyl bromoacetate (34.5 mg, 0.176 mmol). The reaction mixture was stirred at 35° C. for 1.5 h. The reaction mixture was filtered, dried under vacuum and purified by silica gel chromatography (EtOAc/EtOH 5:1) to yield complex 16b (29 mg, 90%). $^1$H NMR (300 MHz, $CD_3CN$, 20° C.) δ=7.93 (s, 1H; $CH_{im}$), 6.90 (s, $CH_{im}$), 4.65 (s, 2H; $CH_2N_{im}$), 3.94-3.25 (m, 1H; CHCO), 3.27-3.23 (q, 2H; $CH_2CH$), 1.45 (s, 9H; tBu); $^{13}$C NMR ($CD_3CN$) δ=181.3, 167.3, 143.1, 135.2, 120.6, 83.8, 52.3, 49.7, 28.5, 28.0, 27.8; MS (ESI): m/z (%): 539.9 (100) [M$^+$], 1076.8 (50); elemental analysis calcd (%) for $C_{15}H_{18}N_3O_7Re$ (538.5): C, 33.43; H, 3.34; N, 7.80; found: C, 33.30; H, 3.85; N, 7.68.

Re Complex 15

To hydrolyze the ester groups, compound 16a (30 mg, 0.057 mmol) was stirred in a solution of methanol (5 mL) and LiOH (0.5 M, 2 ml) overnight at room temperature and compound 16b (15 mg, 0.028 mmol) was stirred in a solution of methylene chloride (2 ml) and trifluoroacetic acid (2 ml) for 2 hours at room temperature. Two crude substances were purified by column chromatography (EtOH/THF/AcOH 10:1:0.1) to yield complex 15 (95% and 90% respectively).

Example 6

Coupling of a Biomolecule to the Carboxylate Group in $[Re(CO)_3]^+$ Protected Histidine and Removal of the $[Re(CO)_3]^+$ Protecting Group (Scheme 4)

Re Complex 17

To the solution of the complex 15 (8 mg, 0.02 mmol) in a mixed solution of $CH_2Cl_2/DMF$ (3:0.2 ml) were added BOP (7.4 mg, 0.02 mmol) and $Et_3N$ (2 µl, 0.02 mmol) at room temperature. After 30 min, a solution of phenylalanine-ethyl ester (4 mg, 0.02 mmol) and $Et_3N$ (2 µl, 0.02 mnol) in $CH_2Cl_2$ (2 ml) was added dropwise to the complex solution by syringe. The reaction mixture was stirred overnight. The reaction solution was concentrated in vacuo. The residue was treated with diethyl ether (2×5 ml). The white solid was dissolved in THF (10 ml) and insoluble solid was filtered off. The filtrate was concentrated in vacuo to provide the ethyl ester of complex 17 (75%). $^1$H NMR (500 MHz, $CD_3CN$, 25° C.): δ=7.8 (s, 1H; $CH_{im}$), 7.34-7.21 (m, 5H; $CH_{ph}$), 6.8 (s, 1H; $CH_{im}$), 4.63-4.59 (m, 1H; CHCO), 4.53 (d, 2H; $CH_2N_{im}$), 4.08 (q, 2H; $CH_2CH_3$), 3.92-3.88 (m, 1H; CH-His), 3.18-3.10 (2×dd, 2H; $CH_2$-His, $CH_2$-Phe), 3.05-2.96 (2×dd, 2H; $CH_2$-His, $CH_2$-Phe), 1.17 (t, 3H; $CH_3$); $^{13}$C NMR (500 MHz, $CD_3CN$, 25° C.): δ=198.1, 196.6, 196.5, 180.4, 170.8, 165.5, 142.0, 136.7, 134.3, 129.4, 128.4, 126.8, 124.9, 120.3, 119.6, 61.2, 54.1, 51.4, 49.2, 37.2, 27.7, 13.4; IR (KBr): $\bar{v}$=2020, 1886, 1733, 1636 cm$^{-1}$; MS (ESI): m/z (%): 659 (100) [M$^+$+H]; elemental analysis calcd (%) for $C_{22}H_{24}N_4O_8Re$ (658.6): C, 40.12; H, 3.67; N, 8.51; found: C, 39.31; H, 3.83; N, 8.25.

Ethyl ester group of the complex was hydrolyzed by stirring the complex in mixed solution of 0.5M LiOH and MeOH (1:2) for overnight at room temperature, as mentioned above, to afford complex 17 quantitatively.

General Procedure for the Oxidation of Rhenium from Complex 17 and 15

A solution of compound 17 or 15 (5 mM in $H_2O$, 500 µl) and acid (HCl, TFA, or acetic) solution (1.0, 0.1, or 0.01M in $H_2O$, 70 µl) were added to a vial, which was sealed then degassed with nitrogen (10 min). $H_2O_2$ (0.43, 0.86, or 1.29M in $H_2O$, 60 µl) was added to the degassed vial, followed by heating the sample at 50° C. Monitoring of the reaction mixture was conducted by HPLC at 250 nm, where the reaction mixture (10 µL) was injected on the HPLC at 4, 8, 24, and 48 hrs or until the rhenium complex was not visible in the spectrum. The effectiveness of the reaction condition was calculated by determining the peak area ratio of the rhenium complex over the formation of perrhenate. When the rhenium complex was no longer observed, the reaction mixture was treated with manganese dioxide to remove residual $H_2O_2$ from the reaction mixture then filtered with a Wattman 0.2 µm filter to yield the uncoordinated ligand in solution to be used in $^{99m}$Tc labeling.

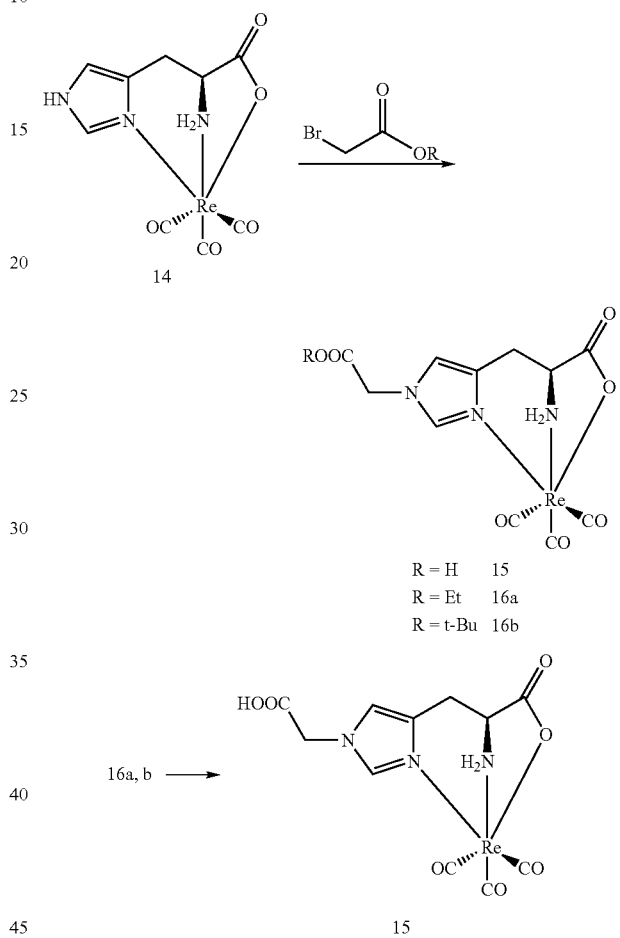

Scheme 3

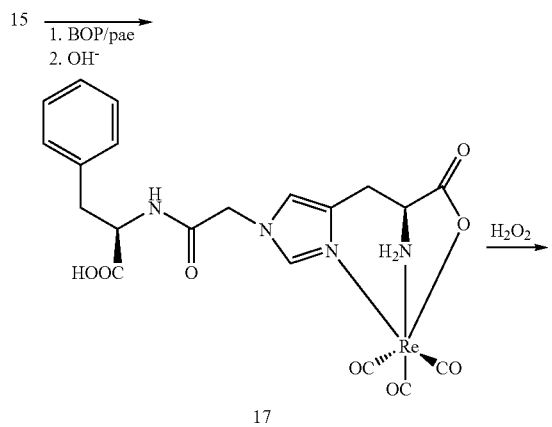

Scheme 4

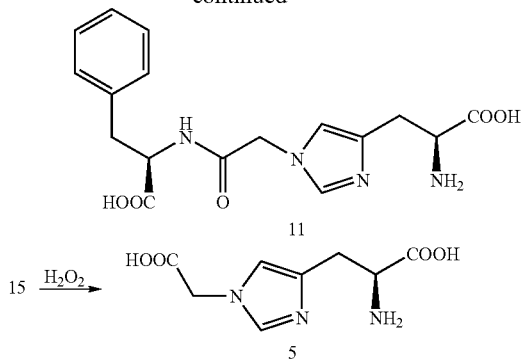

Example 7

Preparation of Histidine with an N^ε pendant —NH$_2$ group (Scheme 5)

3-(1-[3-(9H-Fluoren-9-ylmethoxycarbonylamino)-propyl]-1H-imidazol-4-yl)-2-(3-trimethylsilanyl-propionylamino)-propionic acid methyl ester (molecule 18)

A mixture of 3 (196 mg; 1.0 mmol) and N-Fmoc-3-iodopropylamine (1.22 g; 3.0 mmol) in MeCN (40 ml) was heated at reflux for 4.5 days. When compound 3, urea derivative, was not detectable by TLC, the reaction mixture was concentrated in vacuo, resulting in a white solid. The solid material was redissolved in MeCN (40 ml) and 2-trimethylsilylethanol (355 mg; 3.0 mmol) and dipea (259 mg; 2.0 mmol) were added. The resulting mixture was stirred at RT under N$_2$ for 16 hrs. The solvent was removed in vacuo, followed by purification by column chromatography (silica; EtOAc). Yield: 316 mg (53% over two steps) of a foamy colourless solid Found: C, 62.1; H, 6.2; N, 9.5; Calc. for C$_{31}$H$_{40}$N$_4$O$_6$Si: C, 62.8; H, 6.8; N, 9.5; ν$_{max}$ (KBr)/cm$^{-1}$ 3329br NH, 1730s, 1698vs C=O; δ$_H$ (300.8 MHz; CD$_3$CN) 7.82 (2H, pseudo-d, 2×ArH), 7.64 (2H, pseudo-d, 2×ArH), 7.38 (3H, m, 2×ArH+N$_2$CH$_{His}$), 7.32 (2H, pseudo-t, 2×ArH), 6.79 (1H, s, CH$_{His}$), 6.55 (1H, d, J 7.5, NH), 5.68 (1H, br s, NH), 4.35 (3H, overlapping m, OCH$_2$–Fmoc+C$_α$H), 4.22 (1H, t, J 6.6, OCH$_2$CH–Fmoc), 4.07 (2H, m, CH$_2$), 3.87 (2H, m, CH$_2$), 3.60 (3H, s, OCH$_3$), 2.99 (2H, m, CH$_2$), 2.90 (2H, m, C$_β$H$_2$), 1.85 (2H, m, CH$_2$), 0.93 (2H, m, CH$_2$), 0.01 (s, 9H, Si—(CH$_3$)$_3$). δ$_C$ (CD$_3$CN; 75.47 MHz) 173.7 (C=O$_{ester}$), 157.7, 157.6 (2×C=O$_{amide}$), 145.5, 142.2 (2×ArC$_q$), 138.4 (C$_{His}$), 128.9, 128.3 (2×ArCH), 126.4 (C$_{His}$), 121.2, 118.6 (2×ArCH), 118.1 (C$_{His}$), 66.9, 63.7, 55.3, 52.7, 48.3, 44.9, 38.6, 32.1, 30.1, 18.3, 1.4 (Si(CH$_3$)$_3$); m/z (ESI-pos., MeOH) 343, 371, 533, 593 [M+H]$^+$.

3-[1-(3-amino-propyl)-1H-imidazol-4-yl]-2-(3-trimethyl silanyl-propionylamino)-propionic acid methyl ester (molecule 19)

Compound 18 (255 mg; 0.43 mmol) was dissolved in a 1/1 DMF/NEt$_2$ mixture (8 ml). After the mixture was stirred for 1 hr at RT, the solvent was removed in vacuo. Purification by preparative HPLC (C-18ec column; TFA buffer) afforded compound 19 as a colourless foamy solid as its trifluoroacetate salt. Yield: 190 mg (91%).

δ$_H$ (300.08 MHz; CD$_3$CN) 8.59 (1H, s, N$_2$CH$_{His}$), 7.95 (3H, br, NH$_3^+$), 7.26 (1H, s, CH$_{His}$), 6.56 (1H, d, J 8.4 Hz, NH), 4.43 (1H, m, C$_α$H), 4.24 (2H, t, J 6.9 Hz, CH$_2$), 4.05 (2H, m, CH$_2$), 3.68 (3H, s, OCH$_3$), 3.22 (1H, m, C$_β$H), 3.06 (1H, m, C$_β$H), 2.95 (2H, t, J 6.9, CH$_2$), 2.21 (2H, m, CH$_2$), 0.89 (2H, m, CH$_2$), 0.00 (9H, s, Si—(CH$_3$)$_3$); δ$_C$ (75.47 MHz; CD$_3$CN): 172.7 (C=O$_{ester}$), 162.2 (q, J$_{c, F}$ 34.6, CF$_3$), 157.7 (C=O$_{amide}$), 135.9, 132.4, 120.7 (3×C$_{His}$), 64.0, 54.6, 53.2, 47.0, 37.3, 28.6, 27.6, 18.2 (OCH$_3$, C$_α$, C$_β$+5×CH$_2$), 1.5 (Si—(CH$_3$)$_3$); m/z (ESI-pos.; MeOH): 343.1, 370.8 ([M+H]$^+$, C$_{16}$H$_{30}$N$_4$O$_4$Si requires 371.2) 762 [2M+Na]$^+$.

Example 8

Coupling of Biomolecules to Amino Group in Histidine Derivative (Scheme 5)

a) biotin: D-(+)-Biotin (35 mg; 0.14 mmol) was dissolved in a 4/1 (v/v) mixture of DMF/NEt$_3$ (2.5 ml). To this mixture was added a solution of compound 19 (91 mg; 0.19 mmol) in DMF (2 ml), followed by addition of TBTU (46 mg; 0.14 mmol). After the mixture was stirred for 45 min at RT, it was evaporated to dryness in vacuo. The residue was taken up in 2M NaHCO$_3$ (20 ml) and extracted with CH$_2$Cl$_2$ (3×20 ml). The combined organic layers were washed with 0.5 M HCl (20 ml), H$_2$O (20 ml) and brine (2×20 ml). After removal of the solvent, compound 20 was obtained as a colourless foamy solid. Yield: 67 mg (78%; relative to biotin).

δ$_H$ (300.08 MHz; CD$_3$OD) 7.60 (1H, s, N$_2$CH$_{His}$), 6.95 (1H, s, CH$_{His}$), 4.48 (1H, m), 4.41 (1H, m), 4.29 (1H, m), 4.09 (2H, m), 3.98 (2H, m), 3.69 (3H, s, OCH$_3$), 3.16 (3H, overlapping-m, CH$_2$+H), 2.95-2.78 (5H, overlapping-m, 2×CH$_2$+H), 2.70 (1H, m), 2.19 (2H, m, CH$_2$), 1.93 (2H, m, CH$_2$), 1.63 (4H, m, 2×CH$_2$), 1.43 (2H, m, CH$_2$), 0.94 (2H, m, CH$_2$), 0.01 (9H, s, Si—(CH$_3$)$_3$; δ$_C$ (75.47 MHz; CD$_3$OD): 176.4, 174.3 (C=O$_{ester}$+N$_2$C=O), 166.3, 158.9 (C=O$_{amide}$), 138.5, 138.3, 118.7 (ArC$_{His}$), 64.2, 64.4, 61.7, 57.1, 55.7, 52.8, 45.7, 41.1, 37.4, 36.8, 31.9, 31.1, 29.8, 29.5, 26.8, 18.6 (10×CH$_2$, Cα, Cβ, OCH$_3$, 3×CH), 1.5 (Si—(CH$_3$)$_3$; m/z (FAB$^+$; NBA) 597.2898 (M$^+$, C$_{26}$H$_{45}$N$_6$O$_6$SiS requires 597.2891).

b) to enkephalin: To a solution of purified compound 19 (39 mg; 0.08 mmol) and protected enkephalin (85 mg; 0.08 mmol) in DMF (1.5 ml) and NEt$_3$ (0.5 ml) was added TBTU (25 mg; 0.08 mmol). The mixture was stirred for 45 mins at RT and concentrated to dryness in vacuo. The compound was purified by HPLC (run 1: C8-column; 50 mM TRIS buffer; run 2: C8-column; TFA buffer). Yield: 42 mg (49%) of compound 21 as glassy solid.

δ$_H$ (500.25 MHz; CD$_3$OD) 8.77 (1H, s, N$_2$CH$_{His}$), 7.43 (1H, s, CH$_{His}$), 7.28 (4H, m, 4×ArH), 7.20 (1H, m, ArH), 7.12 (2H, pseudo-d, 2×ArH), 6.90 (2H, pseudo-d, 2×ArH), 4.52 (1H, m, C$_α$H), 4.49 (1H, m, C$_α$H), 4.22-4.09 (7H, overlapping m, 2×C$_α$H+2×CH$_2$), 3.85 (2H, m, CH$_2$-Gly), 3.78 (2H, m, CH$_2$-Gly), 3.73 (3H, s, OCH$_3$), 3.25-3.02 (9H, overlapping m, 2×CH$_2$+3×C$_β$H), 2.84 (1H, m, C$_β$H), 2.04 (1H, m, CH$_2$—CH$_2$—CH$_2$), 1.71 (1H, m, C$_γ$H-Leu), 1.56 (2H, m, C$_β$H$_2$), 1.36 (9H, S, OC(CH$_3$)$_3$), 1.28 (9H, S, OC(CH$_3$)$_3$), 0.94 (3H, d, J 6.3, Leu-CH$_3$), 0.89 (3H, d, J 6.3, Leu-CH$_3$); δ$^c$ (90.5 MHz; CD$_3$OD) 175.5, 175.1, 174.2 172.9, 172.6, 158.7, 158.2 (C=O,), 155.4, 138.3, 136.4, 133.6, 130.9, 130.2, 129.6, 128.0, 125.2, 121.2 (all ArC), 81.0, 79.6 (C$_q$), 64.5, 58.0, 57.5, 54.4, 53.2, 47.6, 44.1, 41.0, 38.1, 38.0, 36.3, 30.8, 29.2, 28.7, 28.2, 25.9, 23.5, 21.7, 18.6, -1.5 (CH, CH$_2$ and CH$_3$;); m/z (FAB$_+$; NBA) 1064.5789 ([M+H]$^+$, C$_{53}$H$_{82}$N$_9$O$_{12}$Si requires 1064.5852)

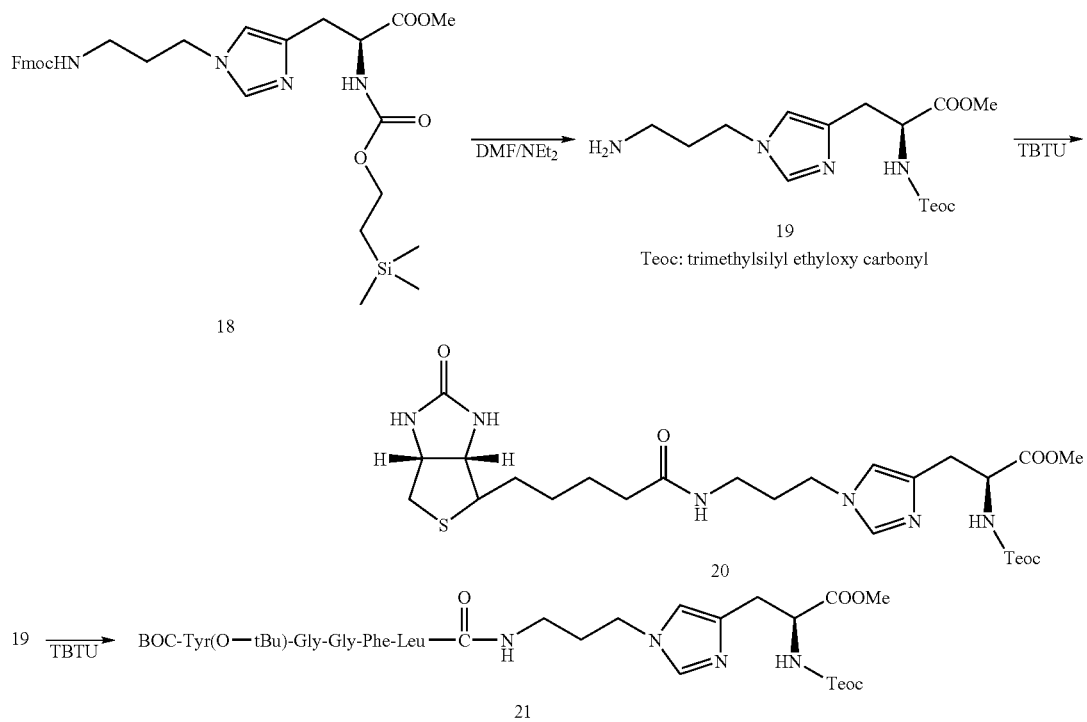

Example 9

Coupling of Two Functional Groups to $N^\epsilon$ and $N^\alpha$ (Scheme 6)

2,6-Bis-tert-butoxycarbonylmethyl-7-methoxycarbonyl-5-oxo-5,6,7,8-tetrahydro-imidazo[1,5-c]pyrimidin-2-ium; bromide (molecule 22)

NaH 13 mg (0.307 mmol) was suspended in dried DMF (2 ml) at 0° C. A solution of compound 3 60 mg (0.307 mmol) in DMF (1 ml) was added slowly dropwise. The reaction mixture was stirred at 0° C. for 30 min and at room temperature for 1 h more until no gas was evolved. The reaction solution was cooled down to 0° C. again. Bromoacetic acid tert-butyl ester 0.07 ml (0.461 mmol) was added by syringe very slowly at cold condition. The solution was stirred at 0° C. for 30 min and at r.t. for 2 hrs more. When the compound 3 was not detectable by TLC, bromoacetic acid tert-butyl ester 0.14 ml (0.921 mmol) was added once more dropwise. The reaction mixture was heated to 70° C. for overnight. The reaction was monitored by TLC. After 15 hours of heating, the solution was cooled down to r.t. and concentrated in vacuo. The crude reside was treated with diethyl ether twice to remove excess of bromide and dried in vacuo. The crude compound 22 was used for next step without further purification. MS (ESI): m/z: 424.56 [M–Br]+

2-[tert-Butoxycarbonylmethyl-(9H-fluoren-9-yl-methoxy carbonyl)-amino]-3-(1-tert-butoxycarbonyl-methyl-1H-imidazol-4-yl)-propionic acid methyl ester (molecule 23)

The crude compound 22 was dissolved in acetonitrile (10 ml) at r.t. Fm—OH 181 mg (0.921 mmol) and DIPEA 0.08 ml (0.461 mmol) were added. After 24 hours of stirring at r.t., the reaction solution was neutralized by adding 1N HCl solution and concentrated under reduced pressure. The residue was dissolved in $CH_2Cl_2$ and extracted with water once and 1N HCl solution once. The organic layer was dried over $Na_2SO_4$, concentrated in vacuo and purified by flash column chromatography afforded compound 23 (yield: 40-50% from compound 3).

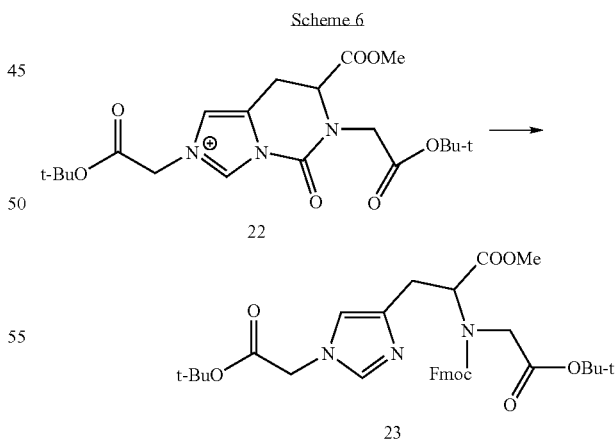

Example 10

Preparation of Activated Histidine Derivative 2-(9H-Fluoren-9-ylmethoxycarbonylamino)-3-(1-pentafluoro phenyloxycarbonylmethyl-1H-imidazol-4-yl)propionic acid methyl ester (molecule 24): Compound 9 (0.198 mmol) was dissolved in THF (3 ml) and pyridine was added to neutralize the solution pH 6-7. Pyridine 0.03 ml (0.396 mmol) was added. Then after a solution of trifluoroacetic acid pentafluoro-phenyl ester (TFA-Pfp) 111 mg (0.396 mmol) in THF (2 ml) was added dropwise by syringe very slowly at r.t. After 19 hours of stirring the reaction mixture at r.t., the solution was concentrated in vacuo. The crude residue was dissolved in dichloromethane and extracted with 0.5N HCl once, 0.5N $Na_2CO_3$ once and brine once. The organic layer was dried over $Na_2SO_4$, concentrated in vacuo, and purified by flash column chromatography afforded compound 24. (Yield: 55%); MS (ESI): m/z: 615.78 $[M+H]^+$

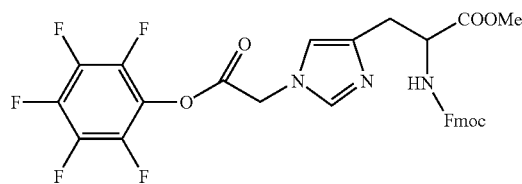

Example 11

General Coupling Procedure of Histidine Derivative to Peptide

Coupling: Compound 9 or 24 was used for the coupling reactions. One of the ligands (normally 0.02-0.08 mmol) was dissolved in DMF and $Et_3N$ or DIPEA (0.03-0.1 mmol) was added as a base. In case of compound 9, BOP or TBTU (normally 0.025-0.09 mmol) was added as a coupling reagent, so that the carboxyl acid group of the ligand was activated in 30 min at room temperature. Then after, a solution of a peptide (normally 0.01-0.02 mmol) in DMF, such as (beta)-hairpin loop peptide, RGD, or bombesin was added dropwise by syringe. In case of compound 24, without coupling reagent, a peptide solution was added right after addition of base. The compound 24 is more suitable when the peptide has a free carboxylic acid group, such as Phe-Gly-OH, Gly-Pro-OH, Gastrin (7 free COOH in structure), or TOCA-OH. Depending on the peptide, the reaction mixture was stirred 2-18 hours. The reaction was monitored by HPLC. When the peptide was not detectable by HPLC, the reaction solution was concentrated in vacuo. The crude residue was purified by preparative HPLC and the product was conformed by MS.

Deprotection: A histidine conjugated peptide (normally 0.003-0.006 mmol) was dissolved in piperidine (1 ml) at room temperature. After 30-40 min of stirring, the reaction mixture was poured into ice-cold water (3 ml). The white solid, fulvine, was filtered and rinsed with water (1 ml). The aqueous solution was concentrated in vacuo to provide white solid as an all, Fmoc and methyl ester, deprotected product that was used for labeling without further purification.

Labeling: A solution of a conjugate ($10^{-3}$ or $10^{-4}$ M in water or phosphate buffer (pH7.4), 100 µl) was added to a vial. Then a solution of $[^{99m}Tc(CO)_3(H_2O)_3]^+$ (900 µl) was added to the vial (total concentration: $10^{-4}$ or $10^{-5}$ M). The solution was heated 90° C. for 30 min to 1 hour. Normally the labeling was done quantitatively in 30 min in concentration of $10^{-4}$ M and 20 to 50% in 30 min in concentration of $10^{-5}$ M.

In case of (beta)-hairpin loop peptide, its conjugate showed quantitative labeling in 30 min even in concentration of $10^{-5}$ M.

Example 12

General Labeling Procedures

A solution of ligand ($10^{-3}$ or $10^{-4}$ M in $H_2O$, 100 µl) obtained from either organic synthesis or through rhenium oxidation pathway was added to a vial, which was then sealed and degassed with a stream of nitrogen gas for 10 min. A solution of $[^{99m}Tc(CO)_3(H_2O)_3]^+$ (900 µl) was added to the vial via syringe and the vial was heated to 70-90° C. for 30 min to yield the corresponding $[^{99m}Tc(CO)_3]^+$ complexes, $[(5)^{99m}Tc(CO)_3]$ and $[(11)^{99m}Tc(CO)_3]$ in high yield via HPLC with radioactive detection. All the results are described in Table 4.

TABLE 4

| Method | Nr. of Ligand | Conc. (M) | Temp. (° C.) | Time (min) | Yield (%) |
|---|---|---|---|---|---|
| Two step labeling | 5 | $10^{-4}$ | 70 | 30 | quantitative |
| | 5 | $10^{-5}$ | 70 | 30 | 91[a] |
| | 5 | $10^{-6}$ | 70 | 30 | 20[b] |
| | 11 | $10^{-4}$ | 90 | 30 | quantitative[c] |
| | 11 | $5 \times 10^{-5}$ | 90 | 30 | quantitative |
| | 11 | $10^{-5}$ | 90 | 30 | quantitative[d] |
| | 11 | $10^{-6}$ | 90 | 30 | 41[e] |
| One pot labeling | 11 | $10^{-4}$ | 90 | 20 | 94 |
| | 11 | $5 \times 10^{-5}$ | 90 | 20 | 96 |
| | 11 | $10^{-5}$ | 90 | 20 | 34[e] |

[a]The labeling was done quantitatively in 1 h. Ligand 5 from the oxidation, at 75° C. for 30 min yield was 85%.
[b]The labeling reached 64% yield after 1.5 h.
[c]Ligand 11 from the oxidation showed 88% yield at 90° C. for 30 min.
[d]Ligand 11 from the oxidation showed 73% yield at 90° C. for 30 min.
[e]The labeling reached more than 65% yield after 1.5 h.

The invention claimed is:
1. A compound comprising:
a histidine derivative derivatized at $N^\epsilon$ with a constituent comprising a biomolecule, wherein the histidine derivative has a formula (X) or (XV):

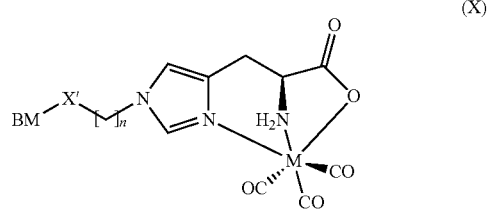

(X)

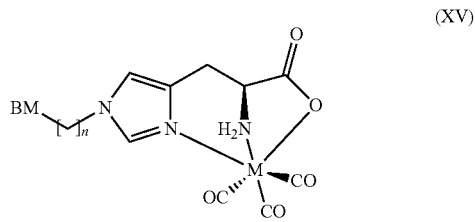

(XV)

wherein BM is a biomolecule, M is radioactive metal, n is an integer from 1 to 5, and X' is a coupling block selected from the group consisting of —N(H)—C(O)—, —C(O)—N(H)—, —O—P(O⁻)(O)—O—, —S-halide-, —S-azide-, —S-pseudohalide-, —S-phosphate-, —S-thiol-, —S-silyl-, —O-halide-, —O-azide-, —O-pseudohalide-, —O-phosphate-, —O-thiol-, —O-silyl-, —N(H)-halide-, —N(H)-azide-, —N(H)-pseudohalide-, —N(H)-phosphate-, —N(H)-thiol- and —N(H)-silyl-.

2. The compound of claim 1, wherein the biomolecule is selected from polypeptides, peptides, amino acids, sugars, and vitamins.

3. The compound of claim 1, wherein M is selected from Re, Tc, and Ru.

4. The compound of claim 3, wherein M is selected from $^{99m}$Tc, $^{188}$Re and $^{97}$Ru and the radioactively labeled metal tricarbonyl is selected from $[^{99m}Tc(OH_2)_3(CO)_3]^+$, $[^{188}Re(OH_2)_3(CO)_3]^+$, and $[^{97}Ru(OH_2)_3(CO)_3]^{2+}$.

5. The compound of claim 1, wherein the biomolecule is —(CH$_2$)n-COO-pentafluorophenyl.

6. The compound of claim 3, wherein the M is selected from $^{188}$Re, $^{99m}$Tc, and $^{97}$Ru.

7. The compound of claim 1, wherein the biomolecule is selected from melanocortin, octreotate, sornastostatin, interleukin-8, CCK, a beta-hairpin loop peptide, neurotensis, biotin, and a monoclonal anti-body.

\* \* \* \* \*